(12) United States Patent
DiMagno et al.

(10) Patent No.: US 7,744,851 B2
(45) Date of Patent: *Jun. 29, 2010

(54) METHODS AND AGENTS FOR PREPARING $^{18}$F-RADIOLABELED FLUORINATING AGENTS

(75) Inventors: Stephen Gregory DiMagno, Lincoln, NE (US); Haoran Sun, Lincoln, NE (US)

(73) Assignee: Board Of Regents Of The University Of Nebraska, Lincoln, NE (US)

( * ) Notice: Subject to any disclaimer, the term of this patent is extended or adjusted under 35 U.S.C. 154(b) by 166 days.

This patent is subject to a terminal disclaimer.

(21) Appl. No.: 11/778,349

(22) Filed: Jul. 16, 2007

(65) Prior Publication Data

US 2008/0019906 A1 Jan. 24, 2008

Related U.S. Application Data

(60) Provisional application No. 60/831,460, filed on Jul. 18, 2006.

(51) Int. Cl.
*A61K 51/04* (2006.01)
*A61K 49/00* (2006.01)
*A61K 101/02* (2006.01)

(52) U.S. Cl. .................. 424/1.11; 564/281; 568/9; 424/9.1; 424/1.65; 424/9.42; 424/9.5; 424/1.89; 424/499

(58) Field of Classification Search .................. None
See application file for complete search history.

(56) References Cited

U.S. PATENT DOCUMENTS 7,592,486 B2 * 9/2009 DiMagno et al. ............ 564/281
2006/0089514 A1 4/2006 DiMagno et al.

OTHER PUBLICATIONS

Christe et al., "Synthesis, Properties, and Structures of Anhydrous Tetramethylammonium Fluoride and its 1:1 Adduct with trans-3-Amino-butenenitrile", Journal of American Chemical Society, 1990, pp. 7619-7625, vol. 112.
Jeong, et al., "Synthesis of No-Carrier Added [18F] Fluoroacetate", Journal of Labelled Compounds and Radiopharmaceuticals, Jan. 9, 1997, pp. 395-399, vol. XXXIX, No. 5, John Wiley & Sons Ltd., Chichester, GB.
Cunico et al., "geminal-Dehalosilyation of alpha-HALO-beta, beta-Dimethylvinyltrimethylsilanes: Generation of Isopropylidene Carbene", Journal of Organometallic Chemistry, 1978, pp. 1-16, vol. 162.
Sharma et al., "Instability of Anhydrous Tetra-n-alkylammonium Fluorides", Journal of Organic Chemistry, 1983, pp. 2112-2114, vol. 48, American Chemical Society.
Extended European Search Report from corresponding European Patent Application No. 07872250.1 dated Jul. 23, 2009.
Ford, W.T.; "Synthesis of Trineopentylamine"; Journal of Organic Chemistry; 1973; pp. 3614-3615; vol. 38, No. 20.
International Search Report for PCT/US07/73623.
Hansch et al.; "A Survey of Hammett Substituent Constants and Resonance and Field Parameters;" Journal; 1991; pp. 165-195; Chem. Rev. 1991, vol. 91, No. 2; American Chemical Society.
Le Bars, Didier; "Fluorine-18 and medical imaging: Radiopharmaceuticals for positron emission tomography;" Journal; 2006; pp. 1488-1493; Journal of Fluorine Chemistry 127; Elsevier, www.elsevier.com/locate/fluor.
Sun et. al.; "Competitive demethylation and substittion in N,N,N-trimethylanilinium fluorides;" Journal; 2007; Cover sheet and pp. 1-7; Journal of Fluorine Chemistry; Elsevier, www.elsevier.com/locate/fluor.
Finn et al.; "Production Considerations for the 'Classical' Pet Nuclides;" Book; pp. 1-38; BNL-68381.

* cited by examiner

*Primary Examiner*—Kamal A Saeed
*Assistant Examiner*—Michael Barker
(74) *Attorney, Agent, or Firm*—Thompson Coburn LLP; Steven M. Ritchey (57) ABSTRACT

The present invention is directed to a method for preparing an anhydrous $^{18}$F-radiolabeled fluorinating agent by a nucleophilic reaction of a hydrated $^{18}$F-radiolabeled fluoride ion source with an unsaturated carrier compound; treating the $^{18}$F-radiolabeled carrier compound to produce a non-aqueous mixture of the $^{18}$F-radiolabeled carrier compound in a solvent; and reacting the $^{18}$F-radiolabeled carrier compound with a nucleophilic composition in a nucleophilic reaction to produce an anhydrous $^{18}$F-radiolabeled fluorinating agent. The present invention is also directed to an anhydrous $^{18}$F-radiolabeled fluorinating agent comprising the formula $[Q_nM]^{x+}(^{18}F^-)_x$. Additionally, the present invention is directed to an $^{18}$F-radiolabeled fluorinated radiopharmaceutical or an $^{18}$F-radiolabeled fluorinated radiotracer prepared by reacting the anhydrous $^{18}$F-radiolabeled fluorinating agent with a drug intermediate. The present invention is further directed to methods for treating a disease or imaging a subject using an $^{18}$F-radiolabeled fluorinated radiopharmaceutical or an $^{18}$F-radiolabeled fluorinated radiotracer.

20 Claims, 2 Drawing Sheets

METHODS AND AGENTS FOR PREPARING $^{18}$F-RADIOLABELED FLUORINATING AGENTS

CROSS REFERENCE TO RELATED APPLICATIONS

This application is claiming the benefit of provisional application No. 60/831,460 under 35 U.S.C. §119(e).

BACKGROUND OF THE INVENTION

The present invention relates to anhydrous $^{18}$F-radiolabeled fluorinating agents and methods for their production and use.

Nuclear medicine uses a variety of radionuclides incorporated into specific compounds for diagnostic imaging and therapeutic applications such as positron emission tomography and cancer treatment. Positron emission tomography (PET) is a non-invasive, functional and metabolic imaging technique by which the decay of a radioactive drug, for example, a radiopharmaceutical or radiotracer, allows one to image body tissues in humans and animals. To conduct a PET scan, a short-lived radioactive tracer isotope that has been incorporated into a metabolically active molecule is administered to a patient or subject. Following a waiting period where the radiotracer becomes concentrated into the tissue(s) of interest, the patient or subject is placed in an imaging scanner. The decay of the radiotracer is monitored by detecting the gamma ray emission resulting from an annihilation event in which a positron collides with an electron giving rise to two photons. Since two gamma rays are produced from each decay event, and because these rays are emitted at almost 180° angles to one another, the location of the radiotracer drug molecule may be ascertained and a three dimensional image of the tissue distribution of the radiotracer drug molecule may be reconstructed. Therapeutic applications use radiopharmaceuticals that deliver a radioactive isotope to a target tissue. As the radioactive isotope decays, the tissue is destroyed.

Synthesis of the radionuclide is a critical component in the manufacture of the finished radiotracer or radiopharmaceutical. One commonly used radioisotope for PET is a radioisotope of fluorine, $^{18}$F. The $^{18}$F radioisotope of fluorine decays with a half life of about 110 minutes. One method for generating $^{18}$F is by bombarding an $^{18}$O labeled water target with a proton beam from a cyclotron causing a (p,n) reaction in the $^{18}$O to produce $^{18}$F as a labeled hydrofluoric acid (HF). The radioactive fluoride ion ($^{18}$F$^-$) must then be rapidly incorporated into a drug molecule by a series of chemical reactions, then purified and administered to a patient or subject. Speed and efficiency are essential for preparing radiopharmaceuticals and radiotracers because they dictate the amount of radioactive isotope available in the radiopharmaceutical or radiotracer and, consequently, the quality of the image and the radiotracer dose. Currently, fluorinated radiopharmaceuticals or radiotracers are prepared most often from $^{18}$F salts, such as potassium fluoride, which are generally produced in a hydrated state after the nuclear reaction. Hydrated fluoride salts, however, are only weakly reactive. Because of the weak reactivity of hydrated fluoride salts, relatively harsh reaction conditions (for example, high temperatures, high boiling point solvents) and relatively expensive cation sequestering agents are employed to incorporate $^{18}$F into a radiopharmaceutical or radiotracer drug intermediate. Additionally, these salts are often "activated" by addition of cryptands, such as Kryptofix 222, to complex the cation and to boost fluoride nucleophilicity. Even using these harsh conditions and expensive agents, some classes of desirable drugs cannot be prepared using $^{18}$F within the extremely short time frame required for these drugs to be useful. Accordingly, there is a need for preparing $^{18}$F-labeled radiopharmaceuticals and radiotracers more efficiently and rapidly than current techniques allow.

U.S. Pat. No. 7,592,486 describes a novel method for producing anhydrous organic fluoride salts and reagents and novel anhydrous organic fluoride salts and reagents. Previously, there was a belief among those skilled in the art that it was unlikely that pure, anhydrous tetraalkylammonium fluoride salts had ever been produced in the case of ammonium ions susceptible to E2 eliminations. The method of U.S. Pat. No. 7,592,486 involves a one-step reaction carried out at low temperatures (−35° C.) to room temperature and uses a fluorinated compound with a large number of fluorine atoms per unit weight, for example, hexafluorobenzene, octafluoronaphthalene, pentafluorobenzonitrile, pentafluoropyridine, and decafluorobiphenyl, to synthesize an anhydrous fluoride salt. The object of the method and the organic fluoride salts and reagents described in U.S. Pat. No. 7,592,486, therefore, is to produce truly anhydrous organic fluoride salts.

BRIEF SUMMARY OF THE INVENTION

Briefly, therefore, the present invention is directed to a method for preparing an anhydrous $^{18}$F-radiolabeled fluorinating agent by reacting a hydrated $^{18}$F-radiolabeled fluoride ion source with an unsaturated carrier compound in a nucleophilic reaction to produce an $^{18}$F-radiolabeled carrier compound and reacting the $^{18}$F-radiolabeled carrier compound with a nucleophilic composition in a second nucleophilic reaction to produce an anhydrous $^{18}$F-radiolabeled fluorinating agent.

The present invention is further directed to a method for preparing an anhydrous $^{18}$F-radiolabeled fluorinating agent by reacting a hydrated $^{18}$F-radiolabeled fluoride ion source with an unsaturated carrier compound in a nucleophilic reaction, wherein at least one $^{18}$F-radiolabeled fluoride ion of the hydrated $^{18}$F-radiolabeled fluoride ion source replaces at least one leaving group of the unsaturated carrier compound to produce an $^{18}$F-radiolabeled carrier compound; treating the $^{18}$F-radiolabeled carrier compound to produce a non-aqueous mixture of the $^{18}$F-radiolabeled carrier compound in a solvent; and reacting the $^{18}$F-radiolabeled carrier compound with a nucleophilic composition in a second nucleophilic reaction, wherein at least one $^{18}$F-radiolabeled fluoride ion of the $^{18}$F-radiolabeled carrier compound is replaced by at least one nucleophile of the nucleophilic composition to produce an anhydrous $^{18}$F-radiolabeled fluorinating agent.

The present invention is also directed to an anhydrous $^{18}$F-radiolabeled fluorinating agent having the formula: $[Q_nM]^{x+}(^{18}F^-)_x$, where M is moiety capable of supporting a formal positive charge, the Q groups are independently varied organic moieties, n is an integer such that the $[Q_nM]$ carries at least one positive charge, and x is an integer defining the number of formal positive charge(s), +, carried by the $[Q_nM]$.

The present invention additionally is directed to a method for imaging a subject by positron electron tomography using an $^{18}$F-radiolabeled fluorinated radiotracer by preparing an $^{18}$F-radiolabeled fluorinated radiotracer prepared by a nucleophilic reaction of a hydrated $^{18}$F-radiolabeled fluoride ion source with an unsaturated carrier compound, wherein at least one $^{18}$F-radiolabeled fluoride ion of the hydrated $^{18}$F-radiolabeled fluoride ion source replaces at least one leaving group of the unsaturated carrier compound to produce an $^{18}$F-radiolabeled carrier compound; treating the $^{18}$F-radiolabeled carrier compound to produce a non-aqueous mixture of the $^{18}$F-radiolabeled carrier compound in a solvent; and reacting the $^{18}$F-radiolabeled carrier compound with a nucleophilic composition in a second nucleophilic reaction, wherein at least one $^{18}$F-radiolabeled fluoride ion of the $^{18}$F-radiolabeled carrier compound is replaced by at least one nucleophile of the nucleophilic composition to produce an anhydrous $^{18}$F-radiolabeled fluorinating agent; reacting the anhydrous $^{18}$F-radiolabeled fluorinating agent with a drug intermediate to produce an $^{18}$F-radiolabeled fluorinated radiotracer; administering the $^{18}$F-radiolabeled fluorinated radiotracer to a subject; and imaging the subject by positron electron tomography.

The present invention further is directed to a method for treating a disease using an $^{18}$F-radiolabeled fluorinated radiopharmaceutical by preparing an $^{18}$F-radiolabeled fluorinated radiopharmaceutical by a nucleophilic reaction of a hydrated $^{18}$F-radiolabeled fluoride ion source with an unsaturated carrier compound, wherein at least one $^{18}$F-radiolabeled fluoride ion of the hydrated $^{18}$F-radiolabeled fluoride ion source replaces at least one leaving group of the unsaturated carrier compound to produce an $^{18}$F-radiolabeled carrier compound; treating the $^{18}$F-radiolabeled carrier compound to produce a non-aqueous mixture of the $^{18}$F-radiolabeled carrier compound in a solvent; and reacting the $^{18}$F-radiolabeled carrier compound with a nucleophilic composition in a second nucleophilic reaction, wherein at least one $^{18}$F-radiolabeled fluoride ion of the $^{18}$F-radiolabeled carrier compound is replaced by at least one nucleophile of the nucleophilic composition to produce an anhydrous $^{18}$F-radiolabeled fluorinating agent; reacting the anhydrous $^{18}$F-radiolabeled fluorinating agent with a drug intermediate to produce an $^{18}$F-radiolabeled fluorinated radiopharmaceutical; and administering the $^{18}$F-radiolabeled fluorinated radiopharmaceutical to a subject.

DETAILED DESCRIPTION OF THE INVENTION

In accordance with the present invention it has been discovered that anhydrous $^{18}$F-radiolabeled fluorinating agents can be prepared by carrying out a nucleophilic reaction of a hydrated $^{18}$F-radiolabeled fluoride ion-containing source with an unsaturated carrier compound to produce an $^{18}$F-radiolabeled carrier compound followed by a nucleophilic reaction of the $^{18}$F-radiolabeled carrier compound with a nucleophilic composition. The anhydrous $^{18}$F-radiolabeled fluorinating agents thus produced are suitable for a variety of applications such as synthesizing $^{18}$F-radiolabeled fluorinated radiopharmaceuticals or $^{18}$F-radiolabeled fluorinated radiotracers. Advantageously, the present invention provides a quick and simple method for synthesis of radiopharmaceuticals and radiotracers because it may be carried out in small volumes, does not require carrying out the reaction at low or high temperatures, and may be carried out in a short period of time. Importantly, the reaction may be performed at temperatures and timescales compatible with the stringent demands of radiopharmaceutical and radiotracer synthesis whereby the $^{18}$F-radiolabel is constantly decaying and obtaining a high specific radioactivity is preferred. Thus, the radiopharmaceuticals or radiotracers may be obtained with a high specific activity. Moreover, because the anhydrous $^{18}$F-radiolabeled fluorinating agents are highly reactive, they provide an advantageous alternative to difficulties encountered while working with the weakly reactive hydrated fluoride salts that are typically used to synthesize $^{18}$F-radiolabeled fluorinated radiopharmaceuticals and $^{18}$F-radiolabeled fluorinated radiotracers, but require harsh reaction conditions, such as high temperatures and high boiling point solvents, and relatively expensive cation sequestering agents. An additional advantage is that the anhydrous $^{18}$F-radiolabeled fluorinating agents may provide enhanced selectivity in substrates that are prone to hydrolysis.

Figure 1:
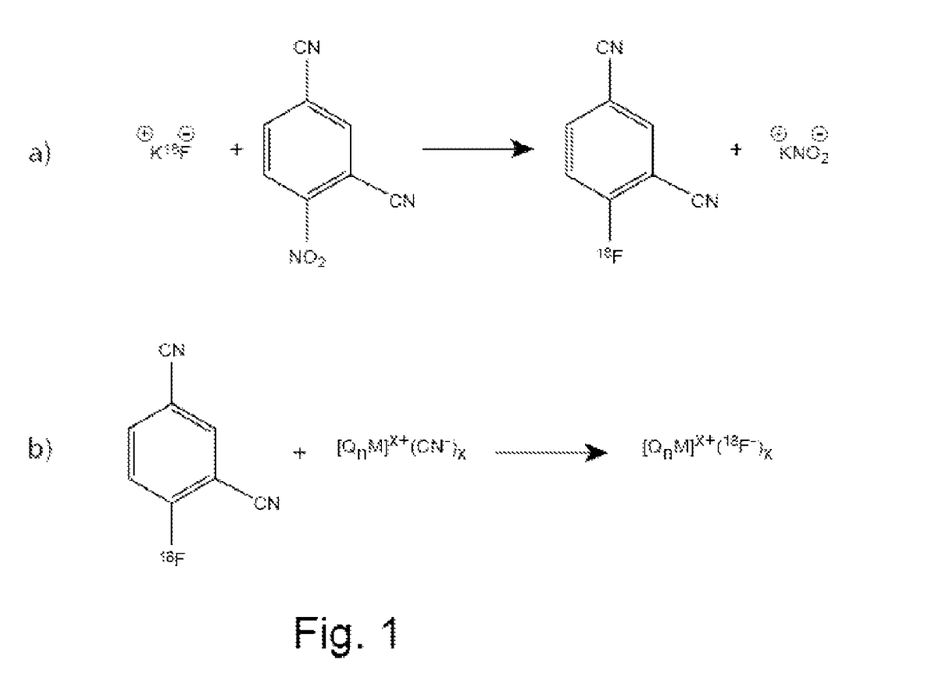
FIG. 1 is a schematic depicting the preparation of an anhydrous $^{18}$F-radiolabeled fluorinating agent by the claimed method.

One aspect of preparing anhydrous $^{18}$F-labeled radiolabeled fluorinating agents according to the present invention is a nucleophilic reaction of a hydrated $^{18}$F-radiolabeled fluoride ion-containing source with an unsaturated carrier compound. According to this reaction, an $^{18}$F-radiolabeled fluoride ion initially formed from the nuclear reaction in a cyclotron is rapidly transformed from a weakly reactive hydrated $^{18}$F-radiolabeled fluoride ion-containing compound into an easily dehydrated $^{18}$F-radiolabeled fluoride carrier compound. Thus, in the nucleophilic reaction, at least one $^{18}$F-radiolabeled fluoride ion of a hydrated $^{18}$F-radiolabeled fluoride ion source replaces at least one leaving group of the unsaturated carrier compound to produce the $^{18}$F-radiolabeled carrier compound. FIG. 1 shows one example illustrating the method of the present invention. Step a of FIG. 1 represents a nucleophilic reaction of a hydrated $^{18}$F-radiolabeled fluoride ion-containing compound, K$^{18}$F, with an unsaturated carrier compound to produce an $^{18}$F-radiolabeled fluoride carrier compound.

The hydrated $^{18}$F-radiolabeled fluoride ion source may be, for example, an ionic compound such as a salt with $^{18}$F$^-$ as the anion. The cation of the hydrated $^{18}$F-radiolabeled fluoride ion source may be, for example, an alkali metal cation such as potassium, sodium, cesium, or lithium. A person skilled in the art will understand that the hydrated $^{18}$F-radiolabeled fluoride ion source may be any compound that is relatively reactive such that the $^{18}$F-radiolabeled fluoride ion may be easily removed. The hydrated $^{18}$F-radiolabeled fluoride ion source may be for example, ionic salts such as, for example, potassium fluoride, sodium fluoride, cesium fluoride, or lithium fluoride. Those skilled in the art will understand that the fluoride salts of a wide variety of cations may be employed to effect fluorination of the carrier compound.

The unsaturated carrier compound may be an aromatic compound or a heteroaromatic compound. The unsaturated carrier compound of the subject nucleophilic reaction has a leaving group that is replaced by the $^{18}$F-radiolabeled fluoride ion of the hydrated $^{18}$F-radiolabeled fluoride ion source pursuant to the reaction. The unsaturated carrier compound preferably may be an aromatic compound wherein a hydrogen is substituted with a leaving group. The leaving group generally departs as an anion, such as for example, a chloro-, bromo-, iodo-, or nitro group. Other similarly substituted polycyclic aromatic compounds may be employed as well. The aromatic compound may be, but is not limited to, for example, chloro-, bromo- or nitro-benzenes, naphthalenes, anthracenes, or pyrenes. Those skilled in the art will understand that many similarly substituted aromatic compounds may be used as the unsaturated carrier compound.

More preferably, the unsaturated carrier compound of the subject nucleophilic reaction may be an electron deficient aromatic compound or an electron deficient heteroaromatic compound. Electron deficient aromatic compounds are compounds bearing at least one electron-withdrawing group. Electron-withdrawing groups are those groups having positive Hammett σm or positive Hammett σp constants. A partial listing of substituent groups is found in Hansch, C. et al., "A survey of Hammett substituent constants and resonance and field parameters," Chemical Reviews (Washington, D.C., United States) (1991), 91(2), 165-195. Electron deficient aromatic compounds may be, but are not limited to, for example, 2-cyanochlorobenzene, 2-cyanonitrobenzene, 1,4-dinitrobenzene, 1,2-dinitrobenzene, 2,6-dicyanochlorobenzene, 2,6-dicyanonitrobenzene. Generally, electron withdrawing groups placed ortho and para to the leaving group are believed have the largest effect upon the rate of fluorine substitution on the carrier compound.

Other substituents, such as, for example, electron-donating groups, may also be present on the aromatic carrier to enhance solubility or facilitate separation of the carrier compound from the reaction mixture. For example, electron-deficient aromatic compounds may bear polymeric substituents.

Heteroaromatic carrier compounds may not necessarily bear electron-withdrawing groups in addition to the leaving group because the heteroatom in the aromatic ring may also facilitate nucleophilic fluorination. The heteroaromatic carrier may be, but are not limited to, for example 2-nitropyridine, 4-nitropyridine, 2-chloropyridine, 4-chloropyridine, 2,6-dichloropyrine, methyl 2-chloroimidazole. Those skilled in the art will understand that a large number of heterocyclic carrier compounds may be used as the carrier compound. For example, in the series of heterocyclic compounds having only nitrogen as the heteroatom in the ring, examples may be, but are not limited to, pyridines, pyrimidines, quinolines, quinolones, isoquinolines, purines, pyrazines, pyrroles, imidzoles, and acridines. One or more different heteroatoms may also be in the ring. Although the above examples stress halide and nitro leaving groups, other leaving groups may be employed, as previously described.

The nucleophilic reaction of the hydrated $^{18}$F-radiolabeled fluoride ion source with the unsaturated carrier compound can take place in a volatile organic solvent. Preferably, the volatile organic solvent is an anhydrous polar aprotic solvent. The anhydrous polar aprotic solvent may be, for example, acetonitrile, tetrahydrofuran, dimethyl sulfoxide, dimethylformamide, dimethylacetamide, hexasmethylposphoric triamide, diethyl ether, dioxane, dimethoxyethane, methyl tert-butyl ether, N-methylpyrolidinone, benzonitrile, nitrobenzene, or butyronitrile. Most preferably, the anhydrous polar aprotic solvent is acetonitrile or dimethyl sulfoxide. Because anhydrous fluoride salts are generally strong bases, readily deprotonated polar aprotic solvents such as acetone, for example, are less useful for this application.

The nucleophilic reaction can take place at room temperature. A person skilled in the art will understand, however, that the reaction may take place at other temperatures depending on the stability of the cation used and/or to increase or decrease the rate of the reaction. Generally, a molar ratio of hydrated $^{18}$F-radiolabeled fluoride ion source to unsaturated carrier compound of between about 1:1 to about 1:1000 is preferred. Typically, amounts of the hydrated $^{18}$F-radiolabeled fluoride ion source employed in the reaction is in the range of about 1 nanomole (nM) to about 1 millimole (mM) and amounts of the unsaturated carrier compound ranges from about 100 nM to about 3 mM. Because the scale of the preparation is small and the total solvent volumes are generally less than about 10 ml, the order of addition generally is not believed to be important and mixing or stirring may not be needed for the reaction to proceed. The reaction may proceed for less than about twenty minutes. Preferably, the reaction proceeds for less than about ten minutes. Advantageously, the reaction may occur at temperatures and timescales compatible with the stringent demands of radiolabeled pharmaceutical and radiotracer synthesis.

The resulting $^{18}$F-radiolabeled carrier compound may be treated to produce a non-aqueous mixture of the $^{18}$F-radiolabeled carrier compound in a solvent. The $^{18}$F-radiolabeled carrier compound is treated by dehydrating and isolating the $^{18}$F-radiolabeled carrier compound and dissolving the $^{18}$F-radiolabeled carrier compound in a non-aqueous solvent. For example, water may be removed from the $^{18}$F-radiolabeled carrier compound produced by any conventional method such as, for example, evaporation, filtration, chromatography, extraction, or combinations thereof. Where water is removed, the complete removal of water is intended. The solvent from the nucleophilic reaction may be removed from the $^{18}$F-radiolabeled carrier compound using conventional methods such as, for example, evaporation, filtration, chromatography, extraction, reduced pressure, or combinations thereof By-products from the nucleophilic reaction may be removed from the $^{18}$F-radiolabeled carrier compound using conventional methods such as, for example, evaporation, filtration, chromatography, capture on a polymeric support, extraction, or combinations thereof The $^{18}$F-radiolabeled carrier compound thus produced then may be dissolved in an anhydrous polar aprotic solvent such as those previously described. This solvent may be the same or different solvent from the nucleophilic reaction described above. The resulting mixture, therefore, is preferably a non-aqueous mixture of the resulting $^{18}$F-radiolabeled carrier compound in anhydrous polar aprotic solvent.

The resulting $^{18}$F-radiolabeled carrier compound may be reacted with a nucleophilic composition in a second nucleophilic reaction to produce an anhydrous $^{18}$F-radiolabeled fluorinating agent. An example of the second nucleophilic reaction is shown in Step b of FIG. 1, in which the $^{18}$F-radiolabeled carrier compound is reacted with a nucleophilic composition to produce an anhydrous $^{18}$F-radiolabeled fluorinating agent. Generally, the nucleophilic composition has the formula $[Q_nM]^{x+}A^-_x$, wherein M is a moiety capable of supporting a formal positive charge, each Q group is an independently varied organic moiety(ies), n is an integer such that the $[Q_nM]$ carries at least one positive charge, x is an integer defining the number of formal positive charge(s), +, carried by the $[Q_nM]$, and $A^-$ is a nucleophile. In this nucleophilic reaction, the $^{18}$F-radiolabeled fluoride ion of the $^{18}$F-radiolabeled carrier compound is replaced by the nucleophile, $A^-$, of the nucleophilic composition to produce an anhydrous $^{18}$F-radiolabeled fluorinating agent having the formula, $[Q_nM]^{x+}(^{18}F^-)_x$.

The moiety, M, of the nucleophilic composition may be any moiety capable of supporting a formal positive charge such as, for example, nitrogen and phosphorus. Thus, in a Lewis dot structure, M will show a positive charge. The moiety may also be certain metal complexes such as for example cobalt, palladium, or other transition metal complexes. In this case, the fluoride may be coordinated to the transition metal ion. A transition metal complex is formed when a transition metal reacts with a variety of molecules or groups that donate electrons to vacant orbitals of the metal.

Each Q group is an independently varied organic moiety (ies). In other words, each Q group on the M is selected independently of the others. The group(s) designated as Q is intended to be more general than the use of "R groups." For example, the "R" designation is generally considered to be an alkyl moiety. Q, however, is intended to encompass, for example, all possible substituent groups including, but not limited to, for example, alkyls, heteroalkyls, aryls, heteroaryls, alkenyls, alkynyls, or polymers. Those skilled in the art will understand that chirality may be introduced either by having different Q groups or by introducing one or more chiral groups in the independently varied organic moieties.

The nucleophile, A, of the nucleophilic composition may be any diffusely charged nucleophile without departing from the scope of the present invention. Generally, a diffusely charged nucleophile is an anionic nucleophile in which the negative charge is delocalized over more than one atom. Generally, the nucleophile is a reagent that forms a chemical bond with its reaction partner (the electrophile) by donating both bonding electrons. All molecules or ions with a free pair of electrons may act as nucleophiles, although negative ions (anions) may generally be more potent than neutral agents. Nucleophiles that may be used for liberating the $^{18}$F-radiolabeled fluoride ion from the $^{18}$F-radiolabeled carrier compound may be, for example, cyanide, thiocyanate, phenoxide, arylalkoxides, thiolates, enolates, isothiocyanate, phosphines, amines, and other nucleophiles recognized by those skilled in the art. The particular nucleophilic composition chosen will depend on the intended use. For example, if the intended use of the final anhydrous $^{18}$F-radiolabeled fluorinating agent is for synthesizing an $^{18}$F-radiolabeled radiopharmaceutical to be administered to a human or animal subject, cyanide may be an undesirable nucleophile because of toxicity considerations. The nucleophilic composition used may be either homogeneous, in other words dissolved completely in solution, or may be heterogeneous, in other words multiphasic. The nucleophilic composition may be associated with a polymer that bears a positive charge, such as, for example, poly(4-vinyl-N,N,N-trialkylanilium) salts.

The second nucleophilic reaction of the $^{18}$F-radiolabeled fluorinated carrier compound with the nucleophilic composition can take place at room temperature. A person skilled in the art will understand, however, that the reaction may be conducted at other temperatures depending on the stability of the cation used and/or to increase or decrease the rate of the reaction. Generally, a molar ratio of hydrated $^{18}$F-radiolabeled fluoride carrier compound to nucleophilic composition of between about 1:1 to about 1:1000 is preferred. Typically, amounts of the hydrated $^{18}$F-radiolabeled fluoride carrier compound employed in the reaction is in the range of about 1 nanomole (nM) to about 1 millimole (mM) and amounts of the nucleophilic ranges from about 100 nM to about 3 mM. Because the scale of the preparation is small and the total solvent volumes are generally less than about 10 ml, the order of addition generally is not believed to be important and mixing or stirring may not be needed for the reaction to proceed. The reaction may proceed for less than about twenty minutes. Preferably, the reaction proceeds for less than about ten minutes. Advantageously, the reaction may occur at temperatures and timescales compatible with the stringent demands of radiolabeled pharmaceutical and radiotracer synthesis.

The resulting anhydrous $^{18}$F-radiolabeled fluorinating agent may be treated to produce a non-aqueous mixture of the anhydrous $^{18}$F-radiolabeled fluorinating agent in a solvent. The solvent from the second nucleophilic reaction may be removed from the $^{18}$F-radiolabeled fluorinating agent using conventional methods such as, for example, evaporation, filtration, chromatography, extraction, reduced pressure, or combinations thereof By-products from the second nucleophilic reaction may be removed from the $^{18}$F-radiolabeled fluorinating agent using conventional methods such as, for example, evaporation, filtration, chromatography, capture on a polymeric support, extraction, or combinations thereof The isolated anhydrous $^{18}$F-radiolabeled fluorinating agent thus produced then may be dissolved in an anhydrous polar aprotic solvent such as those previously described. This solvent may be the same or different solvent from the second nucleophilic reaction described above. The resulting mixture, therefore, is preferably a non-aqueous mixture of the resulting anhydrous $^{18}$F-radiolabeled fluorinating agent in anhydrous polar aprotic solvent. The yield of the anhydrous $^{18}$F-radiolabeled fluorinating agent produced by the method may be between about 65% to about 100%.

Yet another aspect of the present invention is directed to an anhydrous $^{18}$F-radiolabeled fluorinating agent having the formula: $[Q_nM]^{x+}(^{18}F^-)_x$ wherein M is a moiety capable of supporting a formal positive charge, each Q group may be independently varied organic moiety(ies), n is an integer such that the $[Q_nM]$ carries at least one positive charge, and x is an integer defining the number of formal positive charge(s), +, carried by the $[Q_nM]$. The anhydrous $^{18}$F-radiolabeled fluorinating agent is suitable for preparing an $^{18}$F-radiolabeled radiopharmaceutical or an $^{18}$F-radiolabeled radiotracer.

The moiety, M, of the anhydrous $^{18}$F-radiolabeled fluorinating agent may be any moiety capable of supporting a positive charge such as, for example, nitrogen or phosphorus. Thus, in a Lewis dot structure, M will show a positive charge.

Each Q group is an independently varied organic moiety (ies). In other words, each Q group on the M is selected independently of the others. The group(s) designated as Q is intended to be more general than the use of "R groups." For example, the "R" designation is generally considered to be an alkyl moiety. Q, however, is intended to encompass, for example, all possible substituent groups including, but not limited to, for example, alkyls, heteroalkyls, aryls, heteroaryls, alkenyls, alkynyls, or polymers. Those skilled in the art will understand that chirality may be introduced either by having different Q groups or by introducing one or more chiral groups in the independently varied organic moieties.

Advantageously, the anhydrous $^{18}$F-radiolabeled fluorinating agents may be prepared at a temperature and timescale compatible with the stringent demands of radiolabeled pharmaceutical and tracer synthesis. An additional advantage is that the anhydrous $^{18}$F-radiolabeled fluorinating agents are especially nucleophilic allowing their use in introducing the $^{18}$F-radiolabeled fluoride ion into appropriate drug intermediates to form $^{18}$F-radiolabeled fluorinated radiopharmaceuticals or $^{18}$F-radiolabeled fluorinated radiotracers. Moreover, because the anhydrous $^{18}$F-radiolabeled fluorinating agents are highly reactive, they provide an advantageous alternative to difficulties encountered while working with the weakly reactive hydrated fluoride salts that are typically used to synthesize $^{18}$F-radiolabeled fluorinated radiopharmaceuticals and $^{18}$F-radiolabeled fluorinated radiotracers and require harsh conditions, such as high temperatures and high boiling point solvents, and relatively expensive cation sequestering agents. The phrase "weakly reactive" is generally intended to mean having a rate constant for nucleophilic substitution lower than that of Kryptofix KF. Thus, the weakly reactive hydrated $^{18}$F-radiolabeled fluoride salts typically used to synthesize $^{18}$F-radiolabeled fluorinated radiopharmaceuticals and $^{18}$F-radiolabeled fluorinated radiotracers have rate constants for nucleophilic substitution lower than that of Kryptofix KF. The anhydrous $^{18}$F-radiolabeled fluorinating agents according to the present invention are considered to be more reactive because fluoride forms one of the strongest hydrogen bonds known (for example, bond dissociation enthalpies of H—F is about 136 kcal/mol and H—F$_2$ is about 45 kcal/mole). Thus, when water is present, it forms a strong interaction with fluoride, causing a larger activation barrier for any subsequent reaction. In addition to being more reactive, another advantage is that the anhydrous $^{18}$F-radiolabeled fluorinating agents may provide enhanced selectivity in substrates that are prone to hydrolysis.

Figure 2:
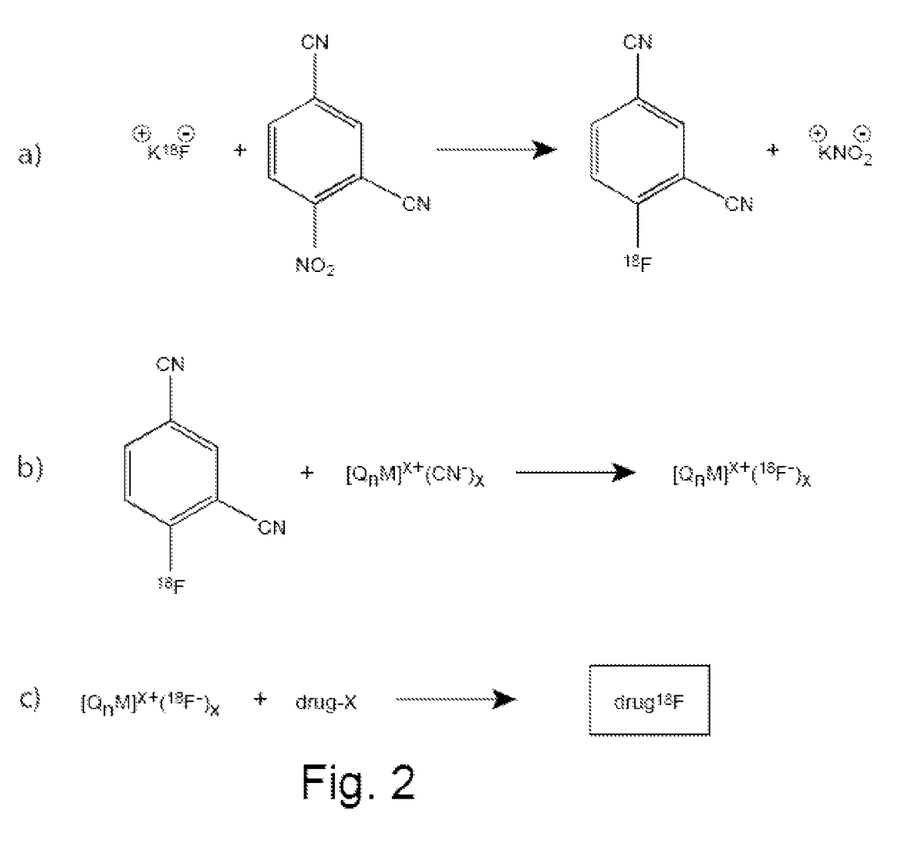
FIG. 2 is a schematic depicting the preparation of an $^{18}$F-radiolabeled fluorinated radiopharmaceutical or an $^{18}$F-radiolabeled fluorinated radiotracer by the claimed method.

An additional aspect of the present invention is directed to the end-use applications of such $^{18}$F-radiolabeled fluorinating agents. For example, the present invention is directed to $^{18}$F-radiolabeled fluorinated radiopharmaceuticals or $^{18}$F-radiolabeled fluorinated radiotracers made using the anhydrous $^{18}$F-radiolabeled fluorinating agent. An example of the method for preparing an $^{18}$F-radiolabeled fluorinated radiopharmaceutical or an $^{18}$F-radiolabeled fluorinated radiotracer is shown in FIG. 2. As shown in Step a of FIG. 2, an $^{18}$F-radiolabeled fluorinated radiopharmaceutical or an $^{18}$F-radiolabeled fluorinated radiotracer is prepared by carrying out a nucleophilic reaction of a hydrated $^{18}$F-radiolabeled fluoride ion source with an unsaturated carrier compound. At least one $^{18}$F-radiolabeled fluoride ion of the hydrated $^{18}$F-radiolabeled fluoride ion source replaces a leaving group of the unsaturated carrier compound to produce an $^{18}$F-radiolabeled fluoride carrier compound. The resulting $^{18}$F-radiolabeled fluoride carrier compound is treated to produce a non-aqueous mixture of the $^{18}$F-radiolabeled fluoride carrier compound in a solvent. For example, water may be removed from the $^{18}$F-radiolabeled fluoride carrier compound produced by the nucleophilic reaction. Water may be removed using any conventional method such as, for example, evaporation, filtration, chromatography, extraction, or combinations thereof The solvent may be removed from the $^{18}$F-radiolabeled carrier compound using conventional methods such as, for example, evaporation, filtration, chromatography, extraction, reduced pressure, or combinations thereof By-products produced in the nucleophilic reaction may be removed from the $^{18}$F-radiolabeled carrier compound using any conventional methods such as, for example, evaporation, filtration, chromatography, capture on a polymeric support, extraction, or combinations thereof The isolated $^{18}$F-radiolabeled carrier compound may be dissolved in an anhydrous polar aprotic solvent such as those previously described. As shown in step b of FIG. 2, the $^{18}$F-radiolabeled fluorinating agent is produced by reacting the $^{18}$F-radiolabeled carrier compound with a nucleophilic composition by carrying out a nucleophilic reaction, wherein the at least one $^{18}$F-radiolabeled fluoride ion of the $^{18}$F-radiolabeled carrier compound is replaced by at least one nucleophile of the nucleophilic composition. As shown in step c of FIG. 2, an $^{18}$F-radiolabeled fluorinated radiopharmaceutical or an $^{18}$F-radiolabeled fluorinated radiotracer is produced by reacting the anhydrous $^{18}$F-labeled fluorinating agent with a drug intermediate (indicated as "drug-X" in step c of FIG. 2). The resulting $^{18}$F-radiolabeled fluorinated radiopharmaceutical or $^{18}$F-radiolabeled fluorinated radiotracer may be used for therapeutic applications, such as cancer treatment, or for imaging, such as positron emission tomography.

A radiopharmaceutical uses the inherent radiation in the compound to treat a disease by delivering the radioactive isotope to the target tissue and destroying the tissue by radioactive decay. A radiotracer is a compound that is generally administered in trace amounts and used in applications such as, for example, imaging. Because the anhydrous $^{18}$F-radiolabeled fluorinating agents may be rapidly prepared and are highly reactive, they are especially nucleophilic allowing for their use in introducing the $^{18}$F-radiolabeled fluoride ion into drug intermediates to form $^{18}$F-radiolabeled fluorinated radiopharmaceuticals or $^{18}$F-radiolabeled fluorinated radiotracers. A drug intermediate may be any non-radioactive pharmaceutical or tracer to which the $^{18}$F-radiolabel is attached to synthesize $^{18}$F-radiolabeled fluorinated radiopharmaceuticals or $^{18}$F-radiolabeled fluorinated radiotracers. Moreover, because the anhydrous $^{18}$F-radiolabeled fluorinating agents of the present invention, and consequently the $^{18}$F-radiolabeled fluorinated radiopharmaceuticals or $^{18}$F-radiolabeled fluorinated radiotracers, may be prepared within an extremely short time frame, the present invention provides an added advantage of improved diagnostic imaging and therapeutic applications such as, positron emission tomography and treatment of cancer.

A further aspect of the present invention is directed to a method for imaging a subject by positron electron tomography using an $^{18}$F-radiolabeled fluorinated radiotracer. The $^{18}$F-radiolabeled fluorinated radiotracer is prepared by carrying out a nucleophilic reaction of a hydrated $^{18}$F-radiolabeled fluoride ion source with an unsaturated carrier compound. At least one $^{18}$F-radiolabeled fluoride ion of the hydrated $^{18}$F-radiolabeled fluoride ion source replaces a leaving group of the unsaturated carrier compound to produce an $^{18}$F-radiolabeled fluoride carrier compound. The $^{18}$F-radiolabeled fluoride carrier compound is treated to produce a non-aqueous mixture of the $^{18}$F-radiolabeled fluoride carrier compound in a solvent. For example, water may be removed from the $^{18}$F-radiolabeled fluoride carrier compound produced by the nucleophilic reaction. Water may be removed using any conventional method such as, for example, evaporation, filtration, chromatography, extraction, or combinations thereof The solvent may be removed from the $^{18}$F-radiolabeled carrier compound using conventional methods such as, for example, evaporation, filtration, chromatography, extraction, reduced pressure, or combinations thereof By-products produced in the nucleophilic reaction may be removed from the $^{18}$F-radiolabeled carrier compound using any conventional methods such as, for example, evaporation, filtration, chromatography, capture on a polymeric support, extraction, or combinations thereof The isolated $^{18}$F-radiolabeled carrier compound may be dissolved in an anhydrous polar aprotic solvent such as those previously described. An $^{18}$F-radiolabeled fluorinating agent is produced by reacting the $^{18}$F-radiolabeled carrier compound with a nucleophilic composition by carrying out a second nucleophilic reaction, wherein the at least one $^{18}$F-radiolabeled fluoride ion of the $^{18}$F-radiolabeled carrier compound is replaced by at least one nucleophile of the nucleophilic composition. An $^{18}$F-radiolabeled fluorinated radiotracer is produced by reacting the anhydrous $^{18}$F-radiolabeled fluorinating agent with a drug intermediate. The drug intermediate may be any non-radioactive tracer to which the $^{18}$F-radiolabel is attached to synthesize the $^{18}$F-radiolabeled fluorinated radiotracer. The $^{18}$F-radiolabeled fluorinated radiotracer is administered to a subject by for example, injection. The subject may be either a human subject or an animal subject. Following a waiting period wherein the $^{18}$F-radiolabeled fluorinated radiotracer becomes concentrated in the tissue(s) of interest, the subject is imaged by positron electron tomography.

Another aspect of the present invention is directed to a method for treating a disease using an $^{18}$F-radiolabeled fluorinated radiopharmaceutical. The $^{18}$F-radiolabeled fluorinated radiopharmaceutical is prepared by carrying out a nucleophilic reaction of a hydrated $^{18}$F-radiolabeled fluoride ion source with an unsaturated carrier compound. At least one $^{18}$F-radiolabeled fluoride ion of the hydrated $^{18}$F-radiolabeled fluoride ion source replaces a leaving group of the unsaturated carrier compound to produce an $^{18}$F-radiolabeled fluoride carrier compound. The $^{18}$F-radiolabeled fluoride carrier compound is treated to produce a non-aqueous mixture of the $^{18}$F-radiolabeled fluoride carrier compound in a solvent. For example, water may be removed from the $^{18}$F-radiolabeled fluoride carrier compound produced by the nucleophilic reaction. Water may be removed using any conventional method such as, for example, evaporation, filtration, chromatography, extraction, or combinations thereof The solvent may be removed from the $^{18}$F-radiolabeled carrier compound using conventional methods such as, for example, evaporation, filtration, chromatography, extraction, reduced pressure, or combinations thereof By-products produced in the nucleophilic reaction may be removed from the $^{18}$F-radiolabeled carrier compound using any conventional methods such as, for example, evaporation, filtration, chromatography, capture on a polymeric support, extraction, or combinations thereof The isolated $^{18}$F-radiolabeled carrier compound may be dissolved in an anhydrous polar aprotic solvent such as those previously described. An $^{18}$F-radiolabeled fluorinating agent is produced by reacting the $^{18}$F-radiolabeled carrier compound with a nucleophilic composition by carrying out a second nucleophilic reaction, wherein the at least one $^{18}$F-radiolabeled fluoride ion of the $^{18}$F-radiolabeled carrier compound is replaced by at least one nucleophile of the nucleophilic composition. An $^{18}$F-radiolabeled fluorinated radiopharmaceutical is produced by reacting the anhydrous $^{18}$F-labeled fluorinating agent with a drug intermediate. The drug intermediate may be any non-radioactive pharmaceutical to which the $^{18}$F-radiolabel is attached to synthesize the $^{18}$F-radiolabeled fluorinated radiopharmaceutical. The $^{18}$F-radiolabeled fluorinated radiopharmaceutical is administered to a subject by for example, injection. The subject may be either a human subject or an animal subject. The $^{18}$F-radiolabeled fluorinated radiopharmaceutical delivers the $^{18}$F-radioisotope to the target tissue and the target tissue is destroyed by radioactive decay.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLES

Example 1

Cyanide-Free Preparation of an $^{18}$F-radiolabeled Fluorinating Agent

Under an atmosphere of dry nitrogen, [$^{18}$F]KF (100 μg) was dissolved in anhydrous dimethyl formamide (1 ml), to which 2-iodoisophthalonitrile (5 mg) was added. The mixture was heated at reflux for 2 minutes and the solvent was removed in vacuo. The residue was taken up in anhydrous ethyl acetate (2 ml) and passed down a column (3×10 mm) of activated silica gel. The column was eluted with additional anhydrous ethyl acetate (2 ml). The resulting solvent of the [$^{18}$F]2-fluoroisophthalonitrile and 2-iodoisophthalonitrile was evaporated off and the aromatic compounds were dissolved in anhydrous acetonitrile (1 ml). This solution was treated with a solution of anhydrous trineopentylmethylammonium (TNPMA) phenoxide and heated at reflux for 5 minutes to form anhydrous [$^{18}$F]TNPMA fluoride.

Example 2

Preparation of Anhydrous Tetrabutylammonium Fluoride (TBAF)

Potassium fluoride (1.16 g; 20 mmol) was reacted with of tetrachloroisophthalonitrile (1.43 g; 5 mmol) in anhydrous dimethyl formamide (15 ml) for 10 minutes at room temperature. The reaction was quenched with 1M HCl (60 ml) and the resulting gray precipitate was collected, washed with deionized water, and dried to yield 5-chloro-2,4,6-trifluoroisophthalonitrile (0.92 g; 85%). In smaller scale experiments, the precipitated 5-chloro-2,4,6-trifluoroisophthalonitrile was dissolved in ethyl acetate-hexane and passed through a silica gel. In a nucleophilic aromatic substitution reaction, 5-chloro-2,4,6-trifluoroisophthalonitrile (21.6 mg; 0.1 mmol) in dimethyl sulfoxide (0.1 ml) was added to a dimethylsulfoxide solution of tetrabutylammonium cyanide (TBACN; 104 mg; 0.4 mmol; 0.4 ml) at room temperature. Anhydrous TBAF formed immediately upon addition.

Example 3

Fluorination of Heterocyclic Substrates using Anhydrous TBAF

Anhydrous TBAF prepared as in Example 2 was used to fluorinate heterocyclic substrates. Anhydrous TBAF was mixed with the naphthyridine antibiotic precursor ethyl 1-(2,4-difluorophenyl)-6-fluoro-7-chloro-1,4-dihydro-4-oxo-1,8-naphthyridine-3-carboxylate using a 1:1 molar ratio in DMSO-$d_6$ (0.5 ml) at room temperature. The reaction proceeded for 10 minutes. Yield of the product determined by integration of $^1$H NMR spectra using the signals from the TBA cation as an internal standard was about 77%.

Anhydrous TBAF prepared as in Example 2 was mixed with 5-chloro-1-methyl-4-nitroimidazole using a 1:1 molar ratio in DMSO-$d_6$ (0.5 ml) at room temperature. The reaction proceeded for 5 minutes. Yield of the 5-fluoro-1-methyl-4-nitroimidazole determined by integration of $^1$H NMR spectra using the signals from the TBA cation as an internal standard was about 80%.

Example 4

Fluorination of Heterocyclic Substrates using TBAF versus Kryptofix 222 KF

Anhydrous TBAF prepared as in Example 2 and Kryptofix 222 KF were used to fluorinate methyl 2,6-dichloronicotinate. Anhydrous TBAF was mixed methyl 2,6-dichloronicotinate in DMSO. The reaction proceeded at room temperature for 10 minutes. Alternatively, Kryptofix 222 KF was mixed with methyl 2,6-dichloronicotinate in DMSO. The reaction was heated at reflux for 10 minutes. Yield of the product using TBAF was >95% compared to the yield of approximately 5% for the product using Kryptofix 222 KF.

Example 5

Prophetic Example for preparing [$^{18}$F]fluorophenyl Methyl Sulfone

Resin-treated target [$^{18}$O]H$_2$O is subjected to proton bombardment, and an aliquot containing 42.2 mCi (1.56 GBq) of

[$^{18}$F]fluoride is transferred to a Vacutainer previously treated with tetrabutylammonium hydroxide (2 µl). The [$^{18}$O]H$_2$O is removed by azeotropic distillation with acetonitrile (3×0.75 ml), N$_2$, and heat. 2-Bromoisophthalonitrile (2.1 mg) is added in anhydrous CH$_3$CN (0.5 mL) and the mixture is heated microwave irradiation (3×20 seconds). The crude mixture is passed through a silica pipet column (50 mg) with CH$_3$CN (3 ml), and the volatile organics are then removed using reduced pressure. Anhydrous tetrabutylammonium phenoxide (3.3 mg) in dimethyl sulfoxide (0.5 ml) is added to the resulting [$^{18}$F]2-fluoroisophthalonitrile and the mixture is heated by microwave irradiation for 20 seconds. 4-Methanesulfonyl-phenyl)-N,N,N-trimethylammonium triflate (1.1 mg; 3.0 µmol) is added to the vessel and dissolved in dimethyl sulfoxide (400 µl). The resulting mixture is heated by microwave irradiation (3×20 seconds). The crude mixture is passed over a silica pipet column (50 mg) with CH$_3$CN (3 mL), and the volatile organics are then removed using reduced pressure. The crude mixture of [$^{18}$F]fluorophenyl methyl sulfone is dissolved in CH$_3$CN (500 ml) and injected through a Teflon filter onto a reverse-phase HPLC column (40% CH$_3$CN/60% H$_2$O, 3.5 ml/min) to obtain pure [$^{18}$F]fluorophenyl methyl sulfone.

In conclusion, the method for preparing the anhydrous $^{18}$F-radiolabeled fluorinating agents of the present invention rapidly transfers the $^{18}$F-radiolabeled fluoride ion of the hydrated $^{18}$F-radiolabeled fluoride ion source formed initially from the nuclear reaction into a much more reactive anhydrous $^{18}$F-radiolabeled fluorinating agent by using an unsaturated carrier compound. Moreover, the resulting anhydrous $^{18}$F-radiolabeled fluorinating agent of the present invention may then be used to introduce the $^{18}$F-radiolabel into appropriate drug intermediates to produce $^{18}$F-radiolabeled fluorinated radiopharmaceuticals or $^{18}$F-radiolabeled fluorinated radiotracers suitable for diagnostic imaging and therapeutic applications such as positron emission tomography and cancer treatment. The entire method allows for the preparation of a wide array of anhydrous $^{18}$F-radiolabeled fluorinating agents on a timescale compatible with the stringent demands of radiopharmaceutical and radiotracer synthesis. Additionally, the resulting anhydrous $^{18}$F-radiolabeled fluorinating agents of the present invention are especially nucleophilic, thus allowing for nucleophilic substitution reactions to be performed on relatively unactivated substrates. In addition to the speed in which the anhydrous $^{18}$F-radiolabeled fluorinating agent of the present invention may be prepared, the high reactivity of the anhydrous $^{18}$F-radiolabeled fluorinating agent provides the added advantage of not requiring the relatively harsh conditions and expensive cation sequestering agents required when using the weakly reactive hydrated fluoride salts used most often for producing radiopharmaceuticals and radiotracers. The benefits possible for the production of fluorinated radiopharmaceuticals and fluorinated radiotracers by using the method of preparing anhydrous $^{18}$F-radiolabeled fluorinating agent and the anhydrous $^{18}$F-radiolabeled fluorinating agents are expected to make the method and the anhydrous $^{18}$F-radiolabeled fluorinating agents preferable over the hydrated $^{18}$F-radiolabeled fluoride salts that are currently available and most often used for synthesizing $^{18}$F-radiolabeled fluorinated radiopharmaceuticals and $^{18}$F-radiolabeled fluorinated radiotracers.

U.S. Provisional Application No. 60/831,460, filed on Jul. 18, 2006, is incorporated by reference herein in its entirety. Further, all other references cited in this specification, including without limitation all patents, journal articles, brochures, manuals, periodicals, texts, manuscripts, website publications, and any and all other publications, are hereby incorporated by reference. The discussion of the references herein is intended merely to summarize the assertions made by their authors and no admission is made that any reference constitutes prior art. Applicants reserve the right to challenge the accuracy and pertinence of the cited references.

It is to be understood that the above description is intended to be illustrative and not restrictive. Many embodiments will be apparent to those of skill in the art upon reading the above description. The scope of the invention should therefore be determined not with reference to the above description alone, but should be determined with reference to the claims and the full scope of equivalents to which such claims are entitled.

When introducing elements of the present invention or an embodiment thereof, the articles "a", "an", "the" and "said" are intended to mean that there are one or more of the elements. The terms "comprising", "including" and "having" are intended to be inclusive and mean that there may be additional elements other than the listed elements. Additionally, it is to be understood an embodiment that "consists essentially of" or "consists of" specified constituents may also contain reaction products of said constituents.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not limiting in a limiting sense.

What is claimed is:

1. A method for preparing an anhydrous $^{18}$F-radiolabeled fluorinating agent having the formula $[Q_nM]^{x+}(^{18}F^-)_x$, wherein:

Q is an organic moiety selected from the group consisting of alkyls, heteroalkyls, aryls, heteroaryls, alkenyls, alkynyls, and polymers;

n is an integer such that $[Q_nM]$ carries at least one formal positive charge;

M is a moiety capable of supporting a positive charge; and x is an integer representing the number of formal positives charge(s), +, carried by the $[Q_nM]$;

the method comprising:

(a) a nucleophilic reaction of a $^{18}$F-radiolabeled fluoride salt with an unsaturated carrier compound in an anhydrous polar aprotic solvent, wherein the unsaturated carrier compound is selected from the group consisting of: an aromatic compound, an electron deficient aromatic compound, a heteroaromatic compound, and an electron deficient heteroaromatic compound;

to produce a $^{18}$F-radiolabeled carrier compound; and (b) reacting the $^{18}$F-radiolabeled carrier compound with a nucleophilic composition having the formula $[Q_nM]^{x+}A_x^n$, wherein A is nucleophile, in a second nucleophilic reaction to yield the anhydrous $^{18}$F-radiolabeled fluorinating agent having the formula $[Q_nM]^{x+}(^{18}F^-)_x$.

2. A method as set forth in claim 1 wherein M is nitrogen, phosphorus, cobalt, palladium, iodine, arsenic, antimony, or a transition metal complex.

3. A method as set forth in claim 1 wherein the anhydrous polar aprotic solvent is acetonitrile, tetrahydrofuran, dimethyl sulfoxide, dimethylformamide, dimethylacetamide, hexasmethylphosphoric triamide, diethyl ether, dioxane, dimethoxyethane, methyl tert-butyl ether, N-methylpyrrolidinone, benzonitrile, nitrobenzene, chlorobenzene, or butyronitrile.

4. A method as set forth in claim 1 wherein the unsaturated carrier compound is an electron deficient aromatic compound or an electron deficient heteroaromatic compound.

5. A method as set forth in claim 1 wherein at least one $^{18}$F-radiolabeled fluoride ion of the $^{18}$F-radiolabeled fluoride salt replaces at least one leaving group of the unsaturated carrier compound by a nucleophilic aromatic substitution reaction.

6. A method as set forth in claim 5 wherein each of the at least one leaving group of the unsaturated carrier compound is a sulfonate, a sulfate, a halide, a carboxylate, a nitrate, a nitrite, a cyanate, an isocyanate, an azide, a thiocyanate, an ether, an amine, a phosphine, or a nitrogen molecule.

7. A method as set forth in claim 1 wherein A is a cyanide, a thiocyanate, a phenoxide, an arylalkoxide, a thiolates, an enolate, an imide anion, amide anion, an isothiocyanate, a phosphine, or an amine.

8. An anhydrous $^{18}$F-radiolabeled fluorinating agent having the formula $[Q_nM]^{x+}(^{18}F^-)_x$, wherein:
M is a moiety capable of supporting a positive charge;
Q is an independently varied organic moiety selected from the group consisting of alkyls, heteroalkyls, aryls, heteroaryls, alkenyls, alkynyls, and polymers;
n is an integer such that $[Q_nM]$ carries at least one formal positive charge; and
x is an integer representing the number of formal positive charge(s), +, carried by the $[Q_nM]$.

9. A method for preparing an $^{18}$F-radiolabeled fluorinated radiopharmaceutical comprising preparing an anhydrous $^{18}$F-radiolabeled fluorinating agent having the formula $[Q_nM]^{x+}(^{18}F^-)_x$ in accordance with the method of claim 1 and reacting the anhydrous $^{18}$F-radiolabeled fluorinating agent with a drug intermediate to produce an $^{18}$F-radiolabeled fluorinated radiopharmaceutical.

10. A method for preparing an $^{18}$F-radiolabeled fluorinated radiotracer comprising preparing an anhydrous $^{18}$F-radiolabeled fluorinating agent having the formula $[Q_nM]^{x+}(^{18}F^-)_x$ in accordance with the method of claim 1 and reacting the anhydrous $^{18}$F-radiolabeled fluorinating agent with a drug intermediate to produce the $^{18}$F-radiolabeled fluorinated radiotracer.

11. An anhydrous $^{18}$F-radiolabeled fluorinating agent prepared by the method of claim 1.

12. An $^{18}$F-radiolabeled fluorinated radiopharmaceutical prepared by the method of claim 9.

13. An $^{18}$F-radiolabeled fluorinated radiotracer prepared by the method of claim 10.

14. A method for imaging a subject by positron electron tomography using an $^{18}$F-radiolabeled fluorinated radiotracer comprising preparing an anhydrous $^{18}$F-radiolabeled fluorinating agent having the formula $[Q_nM]^{x+}(^{18}F^-)_x$ in accordance with the method of claim 1, reacting the anhydrous $^{18}$F-radiolabeled fluorinating agent with a drug intermediate to produce the $^{18}$F-radiolabeled fluorinated radiotracer, administering to a subject the $^{18}$F-radiolabeled fluorinated radiotracer and, imaging the subject by positron electron tomography.

15. A method for treating a disease using an $^{18}$F-radiolabeled fluorinated radiopharmaceutical comprising preparing an anhydrous $^{18}$F-radiolabeled fluorinating agent having the formula $[Q_nM]^{x+}(^{18}F^-)_x$ in accordance with the method of claim 1, reacting the anhydrous $^{18}$F-radiolabeled fluorinating agent with a drug intermediate to produce the $^{18}$F-radiolabeled fluorinated radiopharmaceutical and administering to a subject the $^{18}$F-radiolabeled fluorinated radiopharmaceutical.

16. A method as set forth in claim 14 wherein the subject is a human or an animal.

17. A method as set forth in claim 15 wherein the subject is a human or an animal.

18. A method as set forth in claim 1 wherein the anhydrous polar aprotic solvent is acetonitrile or dimethyl sulfoxide.

19. An anhydrous $^{18}$F-radiolabeled fluorinating agent as set forth in claim 8 wherein M is nitrogen, phosphorus, cobalt, palladium, iodine, arsenic, antimony, or a transition metal complex.

20. An anhydrous $^{18}$F-radiolabeled fluorinating agent as set forth in claim 8 wherein A is a cyanide, a thiocyanate, a phenoxide, an arylalkoxide, a thiolates, an enolate, an imide anion, amide anion, an isothiocyanate, a phosphine, or an amine.

* * * * *

UNITED STATES PATENT AND TRADEMARK OFFICE
CERTIFICATE OF CORRECTION

PATENT NO. : 7,744,851 B2  Page 1 of 1
APPLICATION NO. : 11/778349
DATED : June 29, 2010
INVENTOR(S) : Stephen Gregory DiMagno et al.

It is certified that error appears in the above-identified patent and that said Letters Patent is hereby corrected as shown below:

Col. 14, line 42, please delete "positives" and insert in its place -- positive --

Col. 14, lines 65-66, please delete "methylpyrrolidinone" and insert in its place -- methylpyrolidinone --

Signed and Sealed this

Thirtieth Day of November, 2010

David J. Kappos
*Director of the United States Patent and Trademark Office*